US011814614B2

(12) United States Patent
Kiyama et al.

(10) Patent No.: US 11,814,614 B2
(45) Date of Patent: Nov. 14, 2023

(54) CELL CULTURE DEVICE

(71) Applicant: Hitachi, Ltd., Tokyo (JP)

(72) Inventors: Masaharu Kiyama, Tokyo (JP); Midori Kato, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 426 days.

(21) Appl. No.: 17/086,920

(22) Filed: Nov. 2, 2020

(65) Prior Publication Data
US 2021/0163870 A1  Jun. 3, 2021

(30) Foreign Application Priority Data

Dec. 2, 2019 (JP) ................................. 2019-218179

(51) Int. Cl.
*C12M 1/00* (2006.01)
*C12M 1/04* (2006.01)

(52) U.S. Cl.
CPC ............ *C12M 29/20* (2013.01); *C12M 23/24* (2013.01); *C12M 23/34* (2013.01)

(58) Field of Classification Search
CPC ....... C12M 29/20; C12M 23/24; C12M 23/34
USPC ...................................................... 435/289.1
See application file for complete search history.

(56) References Cited

U.S. PATENT DOCUMENTS

| 2015/0072401 A1* | 3/2015 | Nozaki ................. C12M 37/00 435/303.1 |
| 2017/0022469 A1 | 1/2017 | Kimura et al. |
| 2018/0016534 A1 | 1/2018 | Matsuda |
| 2019/0300837 A1 | 10/2019 | Kiyama et al. |

FOREIGN PATENT DOCUMENTS

| JP | 2007-222120 A | 9/2007 |
| JP | 2016-136928 A | 8/2016 |
| JP | 2016-208864 A | 12/2016 |
| JP | 2017-023131 A | 2/2017 |
| WO | WO-2013183121 A1 * | 12/2013 ............ C12M 25/04 |
| WO | 2018/042710 A1 | 3/2018 |

OTHER PUBLICATIONS

WO2013183121A1 Machine English Translation (Year: 2013).*
Office Action received in Japanese Patent Application No. 2019-218179, drafted Feb. 22, 2023, in 17 pages, with translation.

* cited by examiner

*Primary Examiner* — Michael L Hobbs
*Assistant Examiner* — Lenora A Abel
(74) *Attorney, Agent, or Firm* — Procopio, Cory, Hargreaves & Savitch LLP

(57) ABSTRACT

A cell culture device includes a control unit that includes a first gas supply source, a second gas supply source, and a decompression source, and a culture unit that includes a first container, a second container, a first gas channel that connects a third container, the first gas supply source, the second container to a connection point, a second gas channel, a third gas channel, a first liquid channel, a second liquid channel, a gas-liquid channel, a first valve, a second valve, a third valve, a fourth valve, and a fifth valve.

8 Claims, 6 Drawing Sheets

CELL CULTURE DEVICE

BACKGROUND OF THE INVENTION

1. Field of the Invention

The present invention relates to a cell culture device.

2. Description of the Related Art

In regenerative medicine, which treats disease using own cells or cells of other people, cells taken from the living body is cultured to increase the number of cells or tissues are constructed in an appropriate shape for transplantation treatment. The cell culture for therapeutic use must be carried out in accordance with Good Manufacturing Practice (GMP) in a cell culturing clean room called a cell processing center (CPC). The problem here is that the cell culture is performed manually by a technician, so it takes a lot of labor and cost to prepare the cells for one patient, and there is a risk of biological contamination due to the manual work.

As means for solving these problems, a device for automating the cell culture process in a closed system has been developed. This is to achieve automation of the cell culture process and reduction of biological contamination risk by using a closed culture container that does not require opening and closing of the lid of the culture container.

The main operations that are manually performed during culturing are a cell seeding operation in which a liquid medium with cells or biological samples suspended is introduced into a culture dish, and a liquid medium exchanging operation which is regularly performed during culturing. When adding the liquid medium, a disposable measuring pipette is used, and a predetermined amount of the liquid medium is manually collected from the liquid bottle and added to the culture dish. In an automatic culture device, there is a method for mechanizing the same dispenser and moving means and performing liquid addition similar to the manual operation. However, in this case, the solid phase and the entire gas phase inside the device are installed in a sterile environment. Therefore, the size of the automatic culture device is increased. On the other hand, there has been developed a method in which a pump is used for the dispensing operation, the space from the liquid bottle to the culture container is connected with a disposable tube, and quantifying and liquid feeding are performed at the same time by the pump (see, for example, JP 2007-222120 A). In this case, the inside of the tube used for liquid feeding may be maintained in a sterile state, so that the automation device can be downsized.

SUMMARY OF THE INVENTION

In the method for culturing cells while maintaining the inside of the culture container and the inside of the tube in a sterile state, the exchange-type culture element in which the liquid medium flows and the cells are cultured will be referred to as a culture channel in the following description. Starting with JP 2007-222120 A, the automation device that uses a culture channel can culture cells by reducing the risk of biological contamination, but when the range of culturing becomes wide due to the spread of regenerative medicine, it has been necessary to individually prepare closed culture channels according to the amount and number of cells to be cultivated. For example, if the amount of liquid medium in the culture container changes from several mL to several hundred mL, the size and shape of the culture container must be changed, and the pump to be used for liquid feeding must have a discharge amount corresponding to the required flow rate. In the case of a tube-type pump, it is necessary to prepare tubes having various inner diameters and select an optimum tube diameter. In addition to tubes, it is necessary to prepare various components of the culture channel, but the cost for that is enormous, so there is no choice but to use a certain amount of pump performance and container size. For each automatic culture device, cells that can be cultured within the limited number of cultures and the range of liquid volume have been selected and used.

In addition, there have been two challenges that the operator installs the culture channel on the device before the automatic operation, but it is complicated to install the culture channel and the method for confirming the proper installation of the culture channel has not been established. The former involves complicated operations such as installation of tubes on a large number of valves and installation of tube-type pumps, and if culture containers and bottles are not sealed, they may cause culture medium leakage and biological contamination. Therefore, in order to confirm the proper installation of the culture channel holding the liquid medium inside, for example, an inspection method for introducing a sterile gas and increasing the pressure inside the culture channel to check for the presence of a leak has been often used. However, since the liquid inside may leak during the inspection, it has been the most difficult to confirm the normal installation to the container holding the liquid.

In particular, the tube-type pump used for liquid feeding or drainage is difficult to be used as a built-in component in an exchange-type culture channel because the flow rate of liquid feeding obtained within the output range generated by a fixed motor is fixed.

Therefore, an object of the present invention is to provide a cell culture device that can be easily constructed.

The present inventors have found out the fact that if the pump as a pressure generation source is not an exchange-type pump and a pump installed separately from the culture channel is supplied as a compression source and a decompression source, a culture channel for automatic cell culture can be easily prepared without increasing variations of the pump in the culture channel so as to complete the present invention in consideration of the fact.

A cell culture device according to one embodiment of the present invention includes a control unit that includes a first gas supply source, a second gas supply source, and a decompression source, and a culture unit that includes a first container for containing a culture medium, a second container for culturing cells, a first gas channel that connects a third container for containing a drainage liquid, the first gas supply source, and the second container to a connection point, a second gas channel for connecting the second gas supply source and the first container, a third gas channel for connecting the second container and the decompression source, a first liquid channel for connecting the first container and the second container to the connection point, a second liquid channel for connecting the second container and the third container, a gas-liquid channel for connecting from the connection point to the second container, a first valve provided in the first gas channel, a second valve provided in the second gas channel, a third valve provided in the first liquid channel, and a fourth valve provided in the second liquid channel. The cell culture device may further include a fourth gas channel for connecting between the second container and outside air, a fourth filter provided in the fourth gas channel, a fourth connection portion, of the fourth gas channel, provided on an outside air side of the fourth filter, and a flow meter provided between the fourth connection portion and the outside air. The cell culture device may further include a first filter provided in the first gas channel, a first connection portion, of the first gas channel, provided on a first gas supply source side of the first filter to connect the control unit and the culture unit, a second filter provided in the second gas channel, a second connection portion, of the second gas channel, provided on a second gas supply source side of the second filter to connect the control unit and the culture unit, a third filter provided in the third gas channel, and a third connection portion, of the third gas channel, provided on a decompression source side of the third filter to connect the control unit and the culture unit. The cell culture device may further include a sixth gas channel that is branched from the second gas channel to be connected to outside air, a sixth valve provided in the sixth gas channel, and a fifth filter, of the sixth gas channel, provided on an outside air side of the sixth valve. The cell culture device may further include a seventh valve, of the third gas channel, provided between the third connection portion and the decompression source.

According to the present invention, it has become possible to provide a cell culture device that can be easily constructed.

DESCRIPTION OF THE PREFERRED EMBODIMENTS

Figure 1:
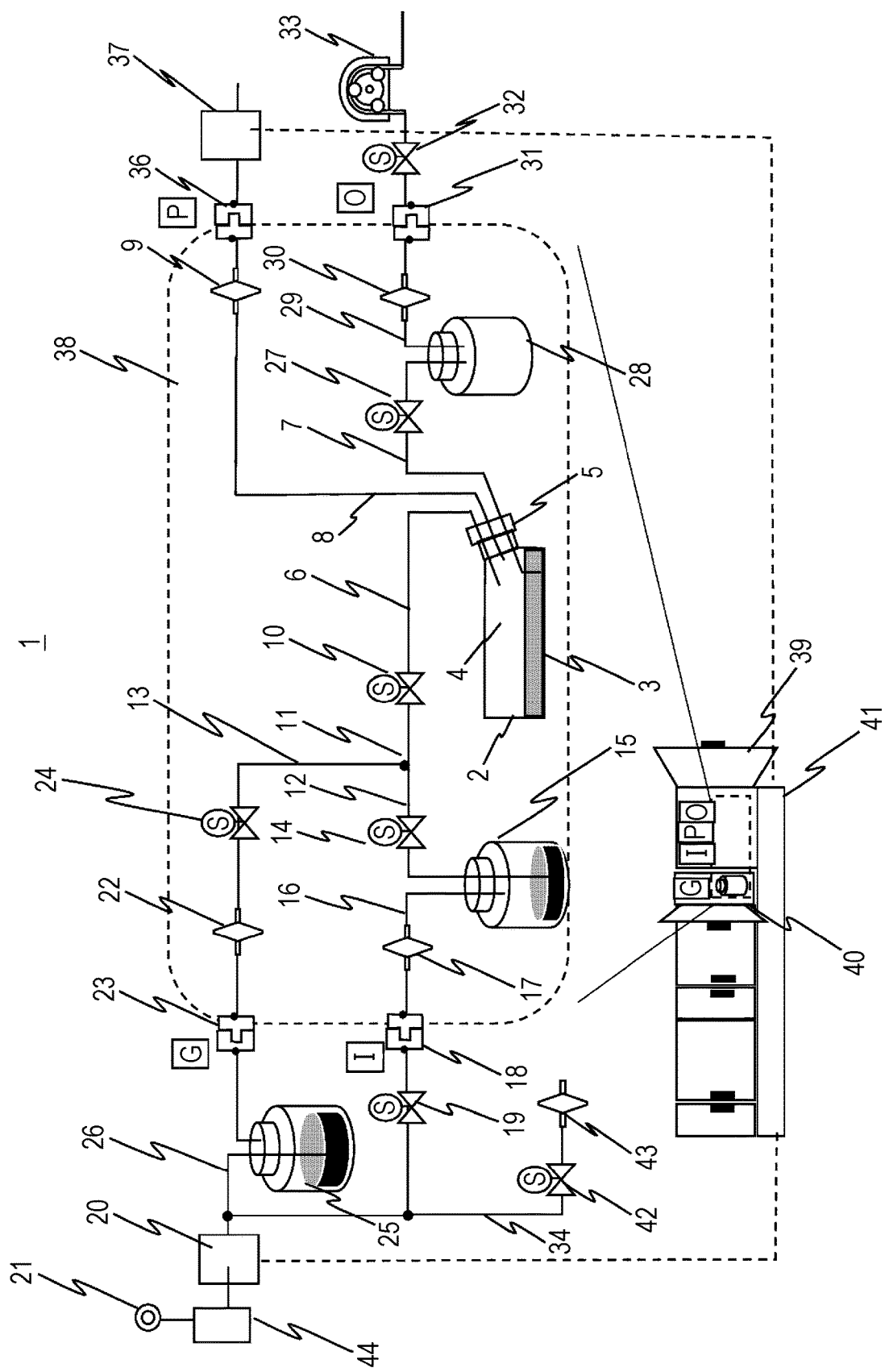
FIG. 1 is a schematic diagram of a cell culture device according to an embodiment of the present invention.

Hereinafter, various embodiments of the present invention will be described with reference to the accompanying drawings. However, the embodiments are described as merely exemplary to realize the present invention, and not limit the technical scope of the present invention. Further, in each of the drawings, the same reference numerals are given to common configurations.

<Configuration of Cell Culture Device>

An embodiment of the cell culture device of the present disclosure includes: a control unit that includes a first gas supply source, a second gas supply source, and a decompression source; and a culture unit that includes a first container for containing a culture medium, a second container for culturing cells, a first gas channel that connects a third container for containing a drainage liquid, the first gas supply source, and the second container to a connection point, a second gas channel for connecting the second gas supply source and the first container, a third gas channel for connecting the second container and the decompression source, a first liquid channel for connecting the first container and the second container to the connection point, a second liquid channel for connecting the second container and the third container, a gas-liquid channel for connecting from the connection point to the second container, a first valve provided in the first gas channel, a second valve provided in the second gas channel, a third valve provided in the first liquid channel, a fourth valve provided in the second liquid channel, a fifth valve provided in the gas-liquid channel, a first filter provided in the first gas channel, a first connection portion, of the first gas channel, provided on a first gas supply source side of the first filter to connect the control unit and the culture unit, a second filter provided in the second gas channel, a second connection portion, of the second gas channel, provided on a second gas supply source side of the second filter to connect the control unit and the culture unit, a third filter provided in the third gas channel, and a third connection portion, of the third gas channel, provided on a decompression source side of the third filter to connect the control unit and the culture unit. The cell culture device 1 of the present disclosure may further include a fourth gas channel for connecting between the second container and outside air, a fourth filter provided in the fourth gas channel, a fourth connection portion, of the fourth gas channel, provided on an outside air side of the fourth filter, and a flow meter provided between the fourth connection portion and the outside air. Hereinafter, the details of the cell culture device will be described with reference to FIGS. 1 to 7.

FIG. 1 is a diagram illustrating the configuration of the cell culture device 1 of a first embodiment. The cell culture device 1 has a gas supply source 21 and a decompression source 33. The cell culture device 1 also has a second container 2 for culturing cells. The second container 2 can hold a liquid medium 3 for cell culture. The second container 2 is not particularly limited in shape as long as it is a cell culture container, and may be a plate, a petri dish or a bottle. The material is not particularly limited, and may be glass or plastic. However, it is preferably plastic because it is easily disposable, and is preferably a bottle because it can be sealed. If the second container 2 is a bottle, it can be opened and closed by a cap 5, and the cap 5 can be airtightly closed during culture. The bottom surface may be coated for cell culture. The unused liquid medium 3 is fed to the second container 2 via a first liquid channel 12 and a gas-liquid channel 6 which are provided so as to penetrate the cap 5. The gas-liquid channel 6 has an open end at a height that is not in contact with the liquid in the second container 2. A gas phase 4 is also delivered through a first gas channel 13 and the gas-liquid channel 6. Further, a second liquid channel 7 provided so as to penetrate the cap 5 has an open end near the bottom of the second container 2. With respect to the used culture medium in the second container 2, the decompression source 33 operates and the second liquid channel 7 becomes a negative pressure, so that the liquid medium 3 inside is discharged. The second container 2 is also provided with a fourth gas channel 8 penetrating the cap 5 to regulate the pressure. The open end of the fourth gas channel 8 is provided at a height that is not in contact with the liquid in the second container 2.

The gas-liquid channel 6 is connected to the connection point 11 via a fifth valve 10. The connection point 11 is connected to the first liquid channel 12 for supplying a culture medium to the second container 2 and the first gas channel 13 for supplying a culture gas to the second container 2. The first liquid channel 12 is provided with a third valve 14 for regulating liquid feeding. The other side of the first liquid channel 12 is connected to a first container 15 holding the liquid medium 3. The first container 15 is a container for storing an unused culture medium, and the shape and material are not particularly limited. The first container 15 is connected to a first liquid channel 12 provided through the lid and a second gas channel 16 for feeding the gas in the first container 15. The inside of the first container 15 can be kept airtight. The first liquid channel 12 provided in the lid has an open end at the bottom of the first container 15 and comes into contact with the liquid to serve as a liquid supply port. The second gas channel 16 has an open end in the first container 15. The open end of the second gas channel 16 is provided at a height that is not in contact with the liquid in the first container. The connection point 11 is provided above the liquid surface of the liquid held in the first container 15.

The second gas channel 16 is connected to the first container 15 from the gas supply source 21 via a second filter 17. The second gas channel 16 is provided with a second connection portion 18 (indicated by I in the drawing) on the gas supply source 21 side of the second filter 17. The connection portion 18 connects the control unit and the culture unit, and is actually connected when the culture is used. The connection portion 18 is, for example, a connector, and may have a male and female structure in which one side may be fixed to a housing of a constant temperature bath 39 surrounding a culture unit 38. The second connection portion 18 is connected via a second valve 19 to a gas control meter 20 for controlling the flow rate of gas to be fed. The second valve 19 adjusts entry of high pressure gas from the gas supply source 21 into the first container 15. A sixth valve 42, which is a normal pressure control valve that allows the internal pressure of the second gas channel 16 to escape to the outside air, may be provided. The sixth valve 42 may be provided with a fifth filter on a sixth gas channel 34 which is branched from the second gas channel 16 and opened to the outside air, and on the outside air side of the sixth valve 42 on the sixth gas channel 34. From the gas supply source 21 which is a gas supply source filled with compressed gas, the gas is supplied to the gas control meter 20 after being controlled to be a predetermined pressure by a pressure regulator 44. The gas supplied from the gas supply source 21 is not particularly limited, but may be, for example, air mixed with 5% $CO_2$ so as to be suitable for cell culture conditions. The supply pressure from the pressure regulator 44 is not particularly limited, but may be, for example, 200 kPa or less, or may be a high pressure of 200 kPa or more when a higher flow rate is required.

The first gas channel 13 for feeding gas from the gas supply source 21 is connected to the second container 2 from the gas supply source 21 via the first valve 24. The first valve 24 adjusts entry of high pressure gas from the gas supply source 21 into the second container 2. The first gas channel 13 is also provided with a first filter 22 and a first connection portion 23 (indicated as G in the drawing) in the gas supply source 21 of the first filter 22. The connection portion 23 connects the control unit and the culture unit, and is actually connected when the culture is used. The first connection portion 23 is, for example, a connector, and may have a male and female structure in which one side may be fixed to a housing surrounding a culture unit. A humidifying bottle 25 may be provided in the first gas channel 13 between the gas supply source 21 and the connection point 11. In that case, the humidifying bottle 25 is connected to the first gas channel 13 and a fifth gas channel 26 connected to the gas supply source 21 while keeping the inside airtight. These gas channels penetrate the lid and open inside. The fifth gas channel 26 may include the gas control meter 20 between the fifth gas channel 26 and the gas supply source 21. Further, the fifth gas channel 26 humidifies the gas from the gas supply source 21 by opening in the liquid in the humidifying bottle 25. On the other hand, the first gas channel 13 has an open end inside the humidifying bottle 25 at a portion that is not in contact with the liquid.

The culture medium used for the cell culture in the second container 2 is fed to a third container 28 for storing the used culture medium through the second liquid channel 7 for feeding the used culture medium. The second liquid channel 7 is connected through the fourth valve 27 so as to penetrate the lid of the third container 28. The third container 28 is provided with a third gas channel 29 penetrating the lid, which connects the third container 28 and the decompression source 33, and the inside can be kept airtight via these. The second liquid channel 7 has one open end inside the third container 28 without coming into contact with the liquid. The third container 28 preferably has a bottle shape that does not deform even when decompressed, and its material is preferably plastic or glass that is difficult to deform. The third gas channel 29 is connected to the decompression source 33 from the third container 28. The third gas channel 29 includes a third filter 30, and a third connection portion 31 (indicated by O in the figure) is provided on the decompression source 33 side of the third filter 30. The third connection portion 31 connects the control unit and the culture unit, and is actually connected when the culture is used. The third connection portion 31 is, for example, a connector, and may have a male and female structure in which one side may be fixed to a housing surrounding a culture unit. A seventh valve 32 may be provided between the decompression source 33 and the third connection portion 31. The seventh valve 32 can be used to turn on/off the decompression and regulate the decompression amount. The gas that has entered the decompression source 33 through the third gas channel 29 may be discharged to the outside air. The decompression source 33 may be a decompression pump.

The fourth gas channel 8 as a pressure regulating pipe is connected to the outside air via a fourth filter 9. The fourth gas channel 8 is provided with a fourth connection portion 36 (indicated as P in the drawing) on the outside air side of the fourth filter 9. The fourth connection portion 36 is connected when the culture is used and is, for example, a connector, and may have a male and female structure in which one side may be fixed to a housing surrounding a culture unit. In the fourth gas channel 8, a flow meter 37 may be provided between the fourth connection portion 36 and the outside air.

In the above configuration, the range surrounded by the broken line in FIG. 1 is the culture unit 38, and the outside thereof is the control unit. The culture unit 38 is attachable to and detachable from each element of the control unit at each connection portion. Further, the culture unit 38 is portable since the first to third containers and the pipes connected to them are integrated.

Figure 7:
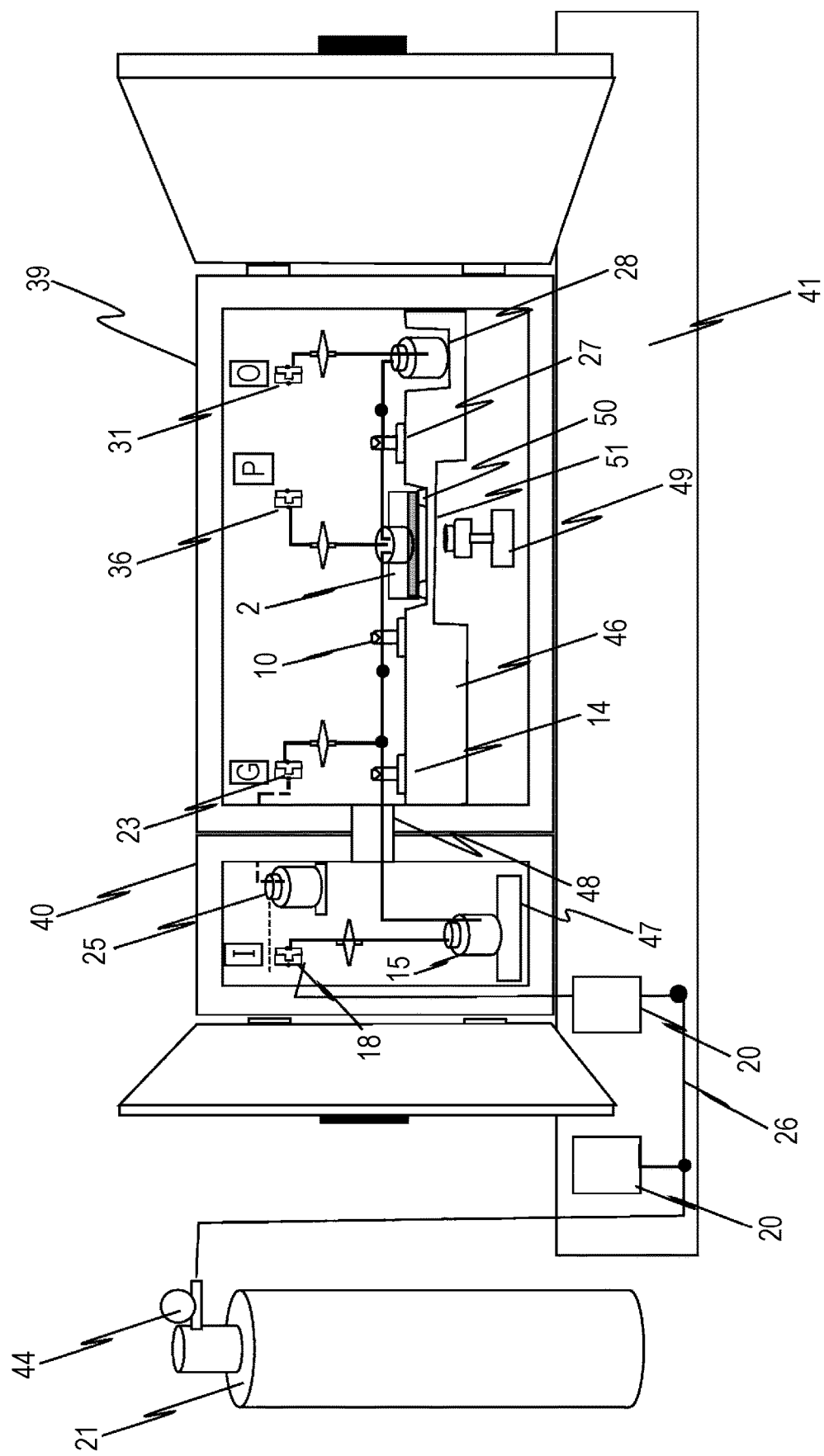
FIG. 7 is a schematic diagram of a cell culture device provided with a culture channel according to an embodiment of the present invention.

As illustrated in FIG. 7, the culture channel 38 may be detachably installed at a predetermined position in the constant temperature bath 39 and a storage 40 having a door structure. Further, the constant temperature bath 39 and the storage 40 may be combined into one set and installed together with a controller 41 for controlling a liquid feeding operation, a gas feeding operation, and a liquid draining operation, which are necessary for the automatic culture. Further, a plurality of sets of constant temperature baths and storages may be integrated in the same manner, and in that case, the controller 41 may perform control necessary for a plurality of automatic cultures in parallel.

A solenoid valve is suitable for the mechanism used for the valve. A general solenoid valve is attached by sandwiching a rubber tube between parts that are opened and closed by the action of an electromagnet, and has a mechanism that elastically deforms the rubber tube when the solenoid valve is turned on/off to open/close the tube.

Any filter can be used as long as it can prevent bacteria, viruses and the like from mixing in the culture unit. For example, a filter having a mesh size of 0.22 μm or less can be preferably used.

The decompression pump used as the decompression source is preferably a roller pump, but other types of pumps such as a diaphragm pump and a gear pump can also be used. A roller pump, which is also called a so-called ironing pump or tube pump, has a mechanism in which a rubber tube is wound around a roller attached to a motor rotation shaft, and the rubber tube is elastically deformed by the rotation of the motor to feed gas or liquid inside.

==Control Method of Cell Culture Device for Culture==

Figure 2:
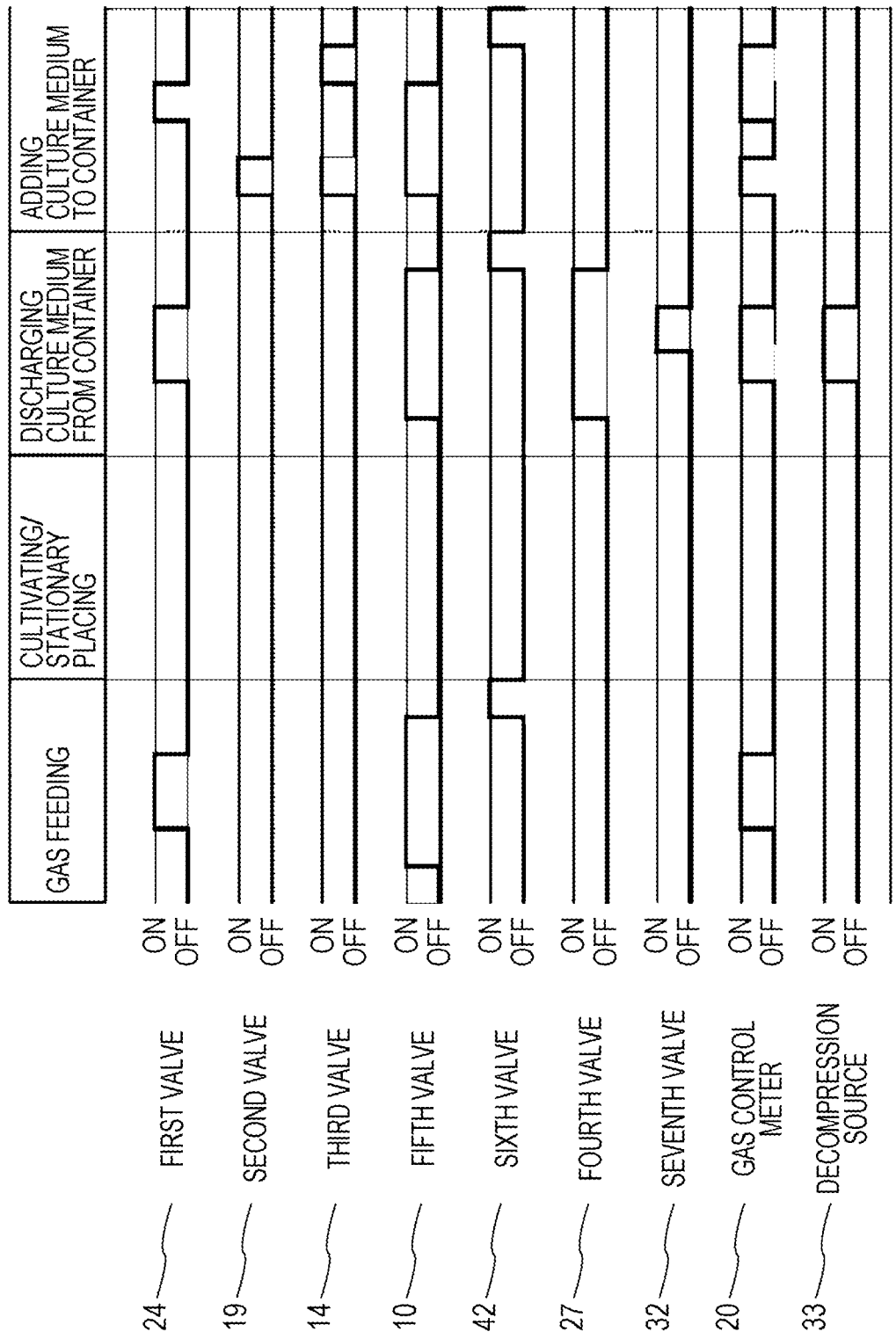
FIG. 2 is a control method of a cell culture device according to an embodiment of the present invention.

FIG. 2 illustrates a control method at the time of culturing and exchanging a culture medium of the cell culture device disclosed in the present specification. The horizontal axis illustrates the operation items and the time axis, and the vertical direction illustrates the operation timings of the seven solenoid valves from the first valve 24 to the seventh valve 32, the gas control meter 20, and the decompression source 33 which are illustrated in FIG. 1. In the initial state, all solenoid valves are OFF and closed, and all pumps are OFF and liquid feeding is stopped. When the gas is fed to the second container 2 of the culture unit 38, if the first valve 24 and the gas control meter 20 are operated after opening the fifth valve 10, a predetermined flow rate of compressed gas begins to be supplied from the gas supply source. The gas is replaced with the gas phase 4 of the second container 2, passes through the fourth gas channel 8, and is released to the outside air. After the air supply for a predetermined time, the first valve 24 and the gas control meter 20 are stopped. If the sixth valve 42 is temporarily opened after the fifth valve 10 is closed, the inside of the humidifying bottle 25 can be maintained at normal pressure.

When draining the liquid medium from the second container 2 for exchanging a culture medium, if the decompression source 33 is operated after opening the fourth valve 27, the inside of the third container 28 connected to the decompression source 33 is depressurized, the second liquid channel 7 is depressurized, and the liquid medium 3 moves from the opening of the second container 2. Accordingly, the fifth valve 10 is opened at the same time as the opening of the fourth valve 27, the first valve 24 is opened, and the gas control meter 20 is operated at the same time as the operation of the decompression source 33. Then, gas is fed into the second container 2 through the gas-liquid channel 6. At the same time, since the air communicates with the outside air through the fourth gas channel 8 and the fourth filter 9, the gas is released and introduced in an amount that exceeds the suction amount of the decompression source 33. In this way, the gas concentration in the second container 2 is prevented from decreasing and the pressure balance in the container is maintained. When a predetermined amount of liquid has been drained, the decompression source 33 is stopped, the fourth valve 27 is closed, and the decompression in the second container 2 is stopped. At the same time, the fifth valve 10 is closed and the pressurization into the second container 2 is closed, so that the inside of the inside of the second container 2 is maintained at normal pressure.

When feeding the liquid medium to the second container 2 for exchanging the culture medium, if the gas control meter 20 is operated after opening the fifth valve 10, the third valve 14, and the second valve 19, the inside of the first container 15 is pressurized, and then the liquid medium reaches the second container 2 via the gas-liquid channel 6. If the fifth valve 10 and the third valve 14 are closed after a fixed amount of liquid has been fed to stop the pressurization of the gas control meter 20, the liquid feeding is stopped, but the liquid medium remains in the gas-liquid channel 6. Next, when the first valve 24 is opened, the liquid medium remaining in the gas-liquid channel 6 reaches the second container 2. At this time, the liquid medium remains between the first liquid channel 12 and the connection point 11, the gas control meter 20 is stopped, the third valve 14 is opened, and then the sixth valve 42 is opened. Then, the liquid medium remaining inside the first liquid channel 12 returns to the first container 15 by a drop. When the sixth valve 42 is temporarily opened, the inside of the first container 15 and the humidifying bottle 25 can be maintained at almost normal pressure.

As a method for quantifying the liquid feeding amount, for example, a fluid equation according to Hagen-Poiseuille's law may be used. Specifically, it is preferable to use a method for calculating an assumed liquid feeding amount from an empirical equation derived from the length of the pipe actually used and the liquid and pressure conditions, in which the length of the gas-liquid channel where the liquid held in the bottle is connected to the second container, the pressure loss, and the viscosity condition of the liquid are used from the relationship between the pressure applied to the pressurized pipe and the pressurization time. Further, a method for feeding the liquid while measuring the weight of the first container 15, which will be described later, is also useful.

Figure 3:
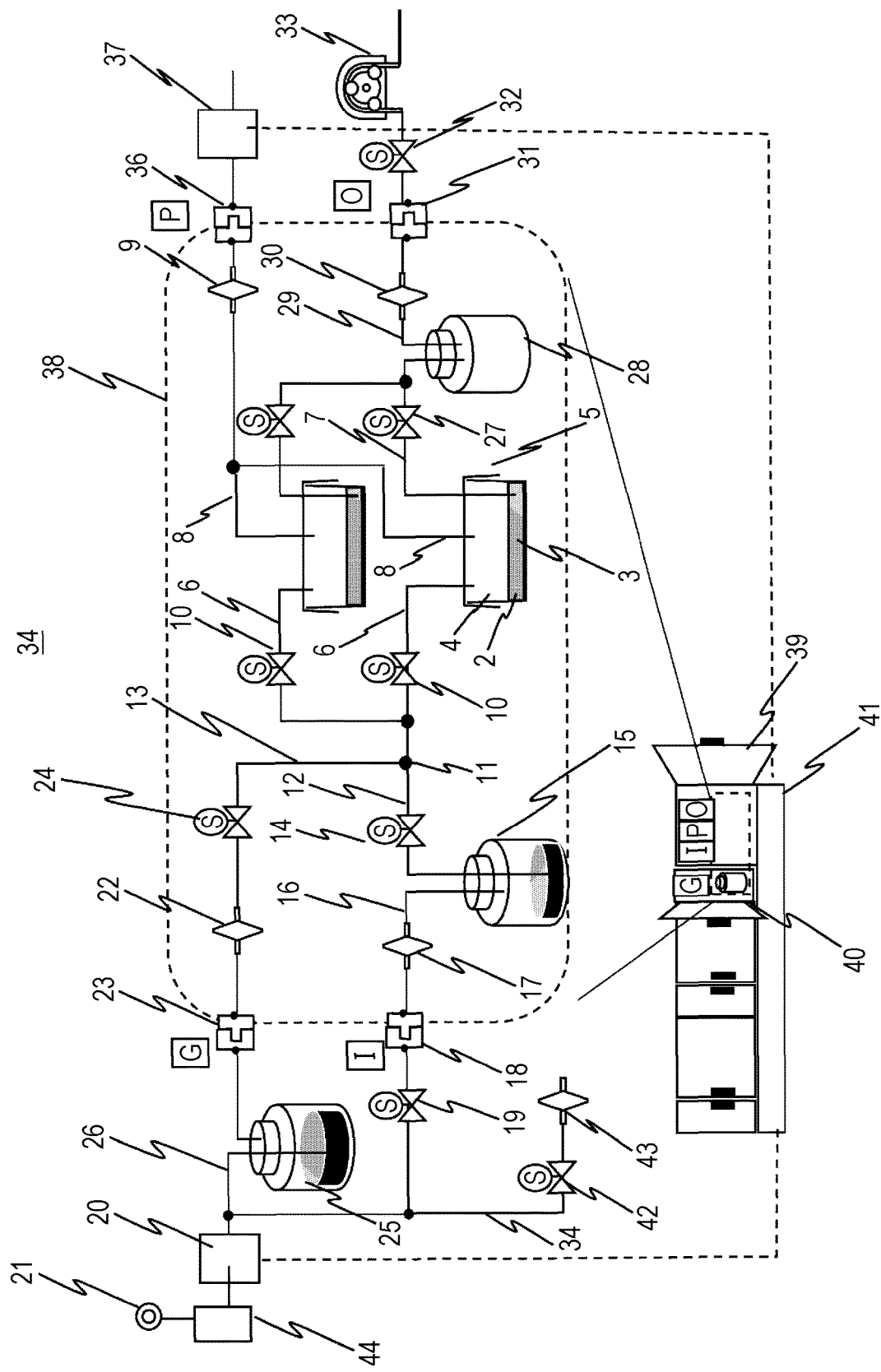
FIG. 3 is a schematic diagram of a second container having a different cap shape according to the embodiment of the present invention.

In FIG. 1, a culture container with a cap called a T-flask is used as the second container 2, whereas in the embodiment of FIG. 3, a culture dish is used as the second container 2 and the container itself has a closed structure. In FIGS. 1 and 3, the same numbers are used for the same components. Even in the shape of a culture dish, the liquid and air can be fed by the gas-liquid channel 6 provided in the cap 5, the liquid can be discharged by the second liquid channel 7, and the pressure of each second container 2 can be regulated from the fourth gas channel 8. When there are a plurality of second containers 2 as illustrated in FIG. 3, a branch is provided in the middle of the connection point 11 and the fifth valve 10 for the gas-liquid channel 6, and the same number of fifth valves 10 as the desired number of second containers 2 may be provided similarly to the installation of the fifth valve 10. Regarding the second liquid channel 7, a branch is provided in the middle of the fourth valve 27 and the third container 28, and the same number of fourth valves 27 as the desired number of the second containers 2 may be configured similarly to the installation of the fourth valve 27. Regarding the fourth gas channel 8, a pipe may be connected by providing a branch in the middle of the cap 5 and the fourth filter 9.

Figure 4:
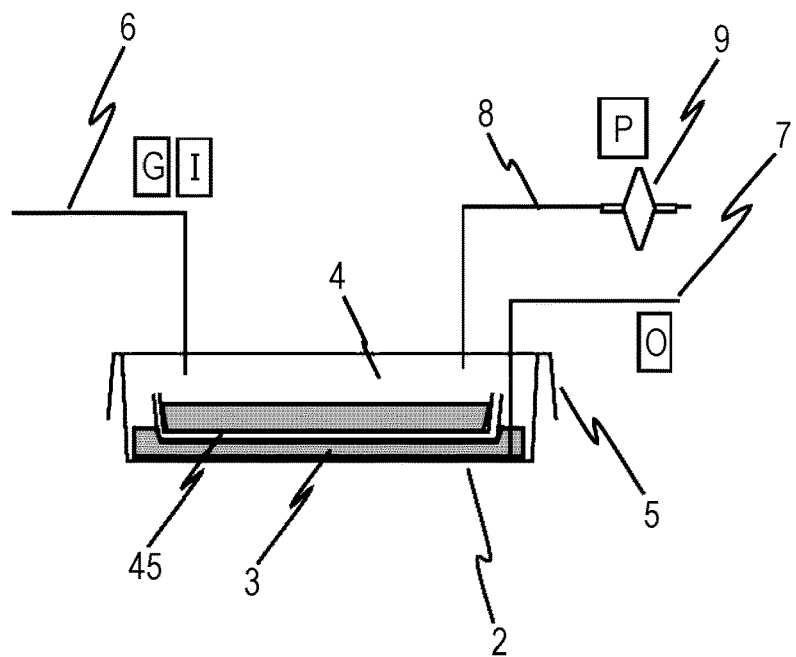
FIG. 4 is a schematic diagram of a second container according to an embodiment of the present invention.

In FIG. 3, the culture surface for holding cells in the second container 2 is one layer of the bottom surface, whereas FIG. 4 illustrates an embodiment in which a combination of the second container 2, which includes an upper container 45 and a lower container, is used as the second container 2. In FIGS. 1 and 4, the same numbers are used for the same components. In this embodiment, the bottom material of the upper container 45 is a substance-permeable membrane, cell culture can be performed on the surface thereof, and cell culture can be performed simultaneously on the surface of the lower culture dish. In the upper container 45 and the second container 2, the same cells may be cultured or different cells may be co-cultured. In this embodiment, the liquid medium 3 and the gas phase 4 can be fed to the upper container 45 by the gas-liquid channel 6 attached to the cap 5. When exchanging the culture medium, if the liquid medium 3 is added to the upper layer after first discharging the lower liquid medium through the second liquid channel 7, the liquid medium 3 passes through the bottom surface of the upper container 45 and moves to the lower layer. Since the gas automatically flows in and out of the fourth gas channel 8 in each of the liquid feeding and liquid discharging, the pressure of the second container 2 is kept constant.

Figure 5:
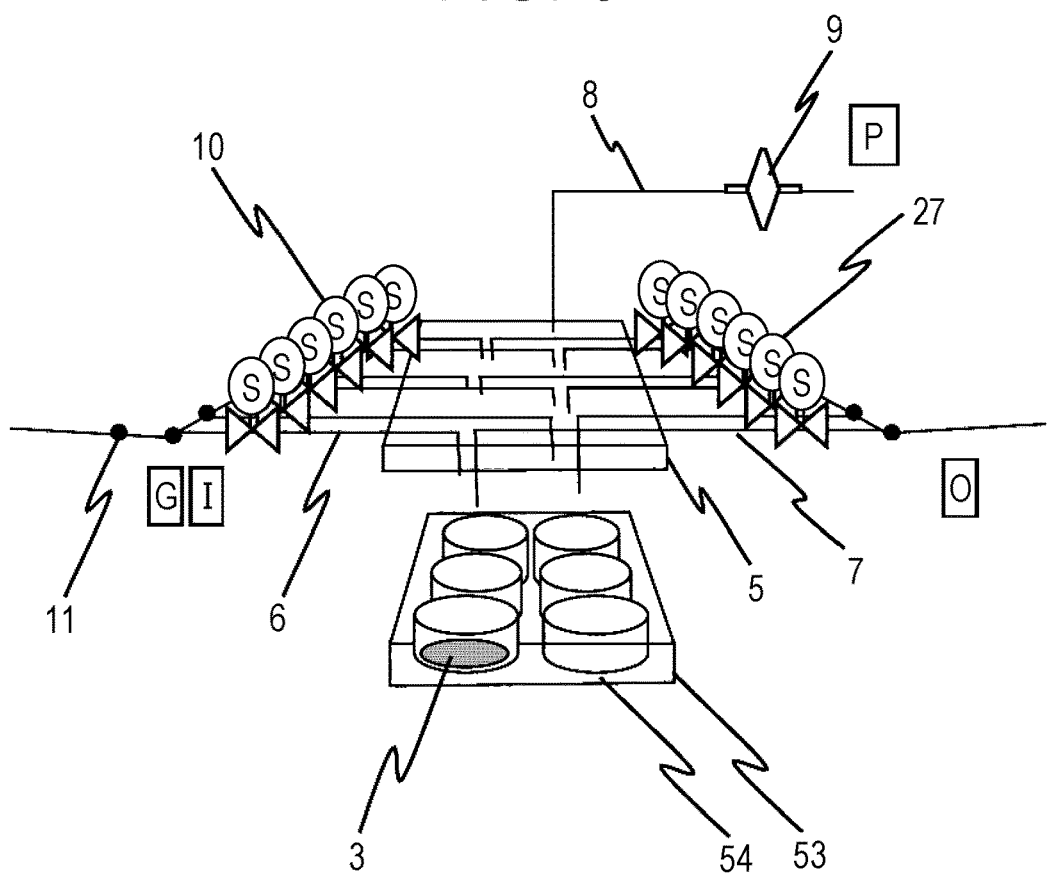
FIG. 5 is a schematic diagram of the second container according to an embodiment of the present invention.

In FIG. 3, the container part for holding cells of the second container 2 is an individual container, whereas FIG. 5 illustrates an embodiment in which the second container 2 has a plurality of wells. In FIGS. 1 and 5, the same numbers are used for the same components. In this embodiment, a culture container generally called a multiwell plate is used, but for example, a multiwell plate having 6 wells or 12 wells is often used. In the culture container having 6 wells as illustrated in FIG. 5, the openings of the six gas-liquid channels 6 provided in the cap 5 are arranged in each well 54, and for each well 54, it is possible to feed the liquid medium 3 and air to the gas phase. Since the same number of gas-liquid channels 6 and fifth valves 10 are prepared according to the number of wells 54, the fifth valve 10 corresponding to the target well is controlled to open when performing liquid feeding or gas feeding to the target wells 54. On the other hand, the openings of the six second liquid channels 7 provided in the cap 5 are disposed near the bottom surface in the well 54, and the liquid can be discharged from the well 54. Since the second liquid channels 7 and the fourth valves 27 are prepared in the same number according to the number of the wells 54, the fourth valve 27 corresponding to the target well 54 opens when the liquid is discharged from the target well 54. On the other hand, in this embodiment, since the respective gas phases of the wells 54 are connected at the upper part of the wells 54, the gas-liquid channel 6 and the fourth gas channel 8 may be provided by one to penetrate the cap 5 to discharge the gas. In this case, it is not necessary to match the well 54 with the fifth valve 10 even in the air supply operation for feeding the gas.

<Operation of Cell Culture>

Figure 6:
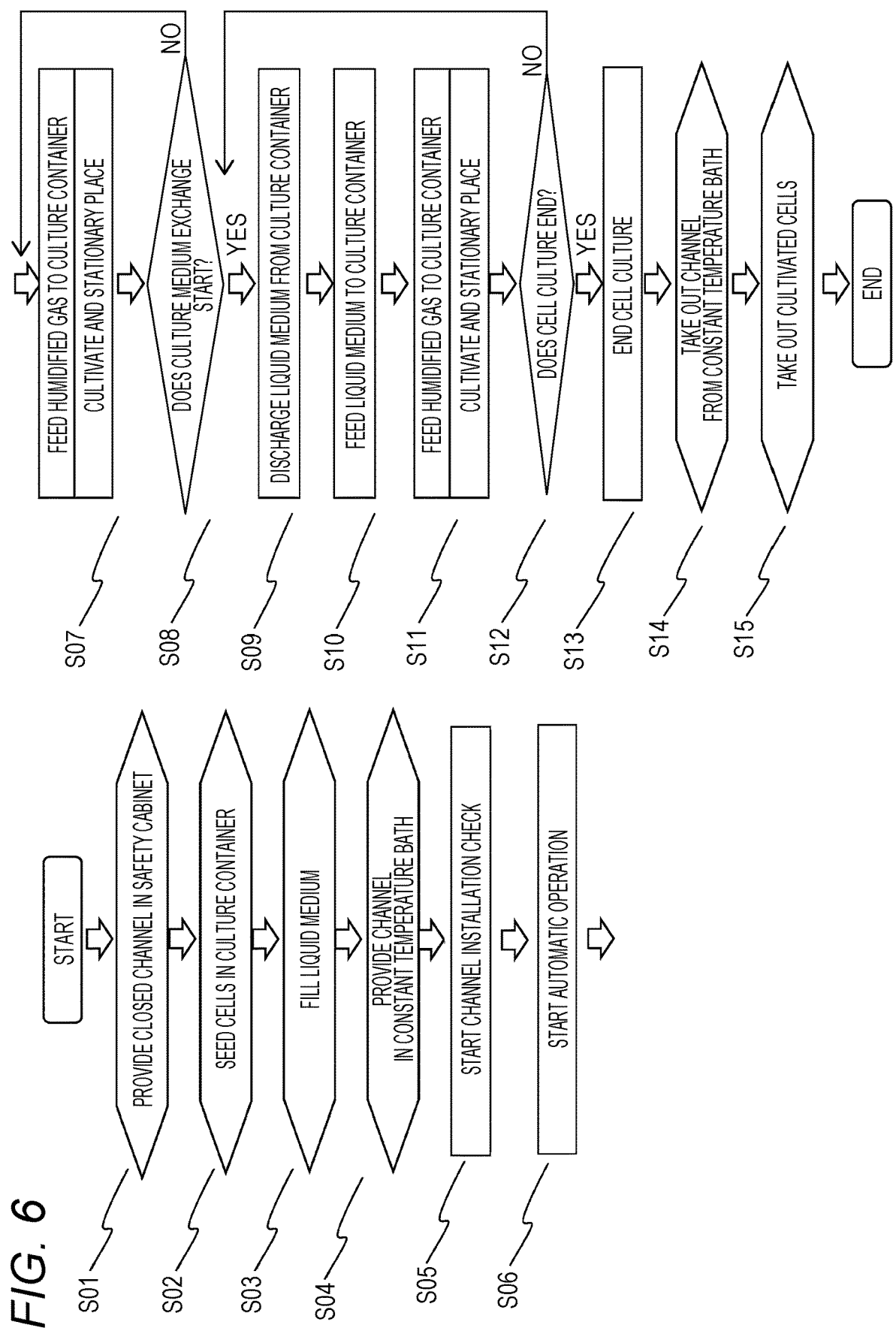
FIG. 6 is a flowchart regarding control of an automatic culture device according to an embodiment of the present invention.

FIG. 6 illustrates a flowchart of the overall operation of a cell culture process using the cell culture device 1 illustrated in FIG. 1. First, a closed channel that is the culture unit 38 is installed in a safety cabinet (S01). Since the interior of the safety cabinet is a sterile space, the cap 5 is opened by hand and a predetermined amount of cell suspension in which cells are suspended in the culture medium is put in the second container 2 to seed the cells (S02). Next, the cap of the first container 15 is opened and the inside is filled with the liquid medium (S03). Each cap is closed, the culture unit 38 is mounted in the constant temperature bath 39, the tubes are installed on all solenoid valves, and then the second connection portion 18, the second connection portion 23, the third connection portion 31, and the fourth connection portion 36 of the culture unit 38 are sequentially connected to the housing of the constant temperature bath 39 (S04).

The cell culture device 1 starts a channel installation confirmation process as to whether the culture unit 38 is normally installed (S05). Specifically, for example, when the values of the gas feeding amount controlled by the gas control meter 20 and the gas discharging amount measured by the flow meter 37 are the same as in the gas supply process in the time chart illustrated in FIG. 2, it may be determined that there is no gas leakage from the culture unit 38 and the normal installation is performed. In that case, if the amount of the flow meter 37 is small, it is determined that the gas is leaking or that the pipe that should not be closed is blocked and abnormally installed. For example, when the closing of the cap 5 of the second container 2 is insufficient, it is possible to detect that the discharge amount is small and the gas is leaking.

Then, the automatic operation is started (S06). The humidified gas (5% $CO_2$-air mixed gas) is fed to the second container 2 at a predetermined time, and then the container is allowed to place stationary to maintain the temperature of the container by a constant temperature machine (S07). This process is repeated until a predetermined start time of exchanging the culture medium. When it is time to exchange the culture medium (S08), the liquid medium is discharged from the second container (S09), and a new liquid medium is fed from the first container 15 to the second container 2 (S10). Further, the gas feeding and the stationary placing are repeated (S11), and when the cell culture end time comes (S12), the automatic operation of the cell culture ends (S13). The culture unit 38 is taken out of the constant temperature machine (S14), and the cultured cells are collected in the safety cabinet (S14). If necessary, the soundness of the cell culture process may be verified by collecting and analyzing the used liquid medium from the drainage bottle 28 and confirming the presence or absence of bacterial growth.

FIG. 7 illustrates a state in which the culture unit 38 is installed in a culture control unit 46 of the cell culture device 1. The culture control unit 46 is provided in the constant temperature bath 39 and incorporates solenoid valve parts such as the third valve 14 and the fourth valve 27. The gas supply source 21 is branched to supply the gas to the plurality of gas control meters 20, but the gas may be shared with an individual cell culture device. An observation mechanism 49 capable of observing cells is installed below the second container 2, and a container holder 50 and an observation window 51 are provided in the culture control unit 46. Further, a weight sensor 47 is configured in the storage 40. If the first container 15 is installed on the weight sensor 47 at a predetermined position, the weight change of the first container 15 and the liquid medium held therein can be measured. It is possible to prevent the tube from being blocked due to the closing of the door at the time of installing the culture unit 38 by disposing a liquid feeding tube in a tube passage 48. The humidifying bottle 25 is always installed inside the storage 40, and a storage unit is provided so that the humidifying water inside can be replenished.

As described above, the culture unit 38 is detachable by the first connection portion 23, the second connection portion 18, the third connection portion 31, and a pressure regulating connector 36, respectively, and the pipes connected to the second container 2, the first container 15, the third container 28, and the pipes connected to the second container 2, which are detachably connected, can be carried together as one body. Therefore, the installation and exchanging of the culture channel are easy.

In addition, multiple constant temperature baths and multiple storages are integrated and installed in the controller 41 that controls the liquid feeding operation, the gas feeding operation, and the liquid draining operation, so that the automatic culture is possible simultaneously in a limited sterile space such as CPC.

Even if there are a plurality of second containers 2 in the culture unit 38, it is possible to provide a device which can automatically culture a plurality of second containers 2 without changing other configurations by providing the same number of fifth valves 10 and fourth valves 27 as the number of containers.

As described with reference to FIGS. 3, 4, and 5, the cell culture device disclosed in the present specification is able to automatically culture various second containers 2 without changing other configurations even if the second container 2 has the shapes of a culture container with a cap called a T-flask, a culture dish, and a container consisting of the upper and lower containers according to the application, even in a culture container called a multiwell plate, and even if the installation and the number of components around the container are changed.

Further, as illustrated in the flowchart of the cell culture process using the cell culture device 1 in FIG. 6, a manual cell seeding process is performed after the culture unit 38 is installed in the safety cabinet, and then the automatic device can perform the channel installation confirmation process as to whether the culture unit 38 is normally installed. Therefore, the automatic culture can be executed reliably. Especially when the liquid is held in the second container or the first container, there is a possibility that unintended high pressure is applied to the inside to eject the liquid inside. However, in the present application, the gas is fed in a state when ventilating using a passage of discharging the gas to the atmosphere. Therefore, there is less risk of applying high pressure to the culture containers or cells, and the normality of the installation of the culture channel can be confirmed.

The fourth gas channel 8 for regulating the pressure of the second container 2 is configured to be discharged from the constant temperature bath 39 to the outside air, and the humidified exhaust gas does not remain in the constant temperature bath 39. Therefore, there is an advantage that the inside of the constant temperature bath 39 can be kept dry. This can reduce the risk of corrosion of metal parts inside the constant temperature bath 39.

Further, since the culture control unit 46 for installing the culture unit 38 is installed in the constant temperature bath 39, and the first container 15 for holding the liquid medium is installed in the storage 40, the cell culture can be maintained at a constant temperature and the liquid medium can be held at room temperature. Therefore, the cell culture can be performed stably.

What is claimed is:

1. A cell culture device comprising:
    a control unit that includes a gas supply source, a connection to outside air, a humidifying bottle, and a decompression source; and
    a culture unit that includes:
        a second container for culturing cells in a culture medium,
        a first container configured to contain an unused culture medium for supplying the unused culture medium to the second container,
        a third container for containing culture medium discharged from the second container,
        a first connection portion configured to connect the culture unit to the gas supply source of the control unit via the humidifying bottle,
        a second connection portion configured to connect the culture unit to the gas supply source,
        a third connection portion configured to connect the culture unit to the decompression source,
        a fourth connection portion configured to connect the culture unit to the connection to the outside air,
        a third gas channel that connects the third container to the third connection portion to generate negative pressure in the third container when a seventh valve provided between the third container and the decompression source is open,
        a third filter provided in the third gas channel between the third container and the third connection portion,
        a second liquid channel that connects the third container to the second container allowing the culture medium to be discharged based on the negative pressure generated in the third container,
        a fourth gas channel for connecting the second container to the outside air via the fourth connection portion for maintaining a pressure balance in the first container,
        a second gas channel that connects the first container to the gas supply source via the second connection portion,
        a first liquid channel connecting the first container to a connection point,
        a first gas channel connecting the first connection portion to the connection point,
        a gas-liquid channel for connecting the connection point to the second container,
        a fourth valve provided in the second liquid channel,
        a third valve provided in the first liquid channel,
        a first valve provided in the first gas channel, and
        a fifth valve provided in the gas-liquid channel.

2. The cell culture device according to claim 1, further comprising:
    a fourth filter provided in the fourth gas channel between the second container and the fourth connection portion;
    a second filter provided in the second gas channel between the first container and the second connection portion; and
    a first filter provided in the first gas channel between the first valve and the first connection portion.

3. The cell culture device according to claim 1, further comprising:
    a flow meter provided between the fourth connection portion and the outside air.

4. The cell culture device according to claim 1, further comprising:
    a branched gas channel comprising an unbranched portion of the branched gas channel connecting the gas supply source to a branching point, a first branched portion of the branched gas channel comprising a fifth gas channel connecting the branching point to the humidifying bottle, a second branched portion of the branched gas channel connecting the branching point to the second connection portion, and a third branched portion of the branched gas channel comprising a sixth gas channel connecting the branching point to the outside air;
    a second valve provided in the second branched portion of the branched gas channel between the second connection portion and the branching point;
    a sixth valve provided in the third branched portion of the branched gas channel comprising the sixth gas channel; and
    a fifth filter, of the sixth gas channel, provided on an outside air side of the sixth valve.

5. A method of culturing cells using the cell culture device of claim 4, comprising:

during a first time period associated with discharging the culture medium from the second container,
   opening the seventh valve, the fourth valve, the fifth valve, and the first valve to allow flow in a first direction through the third gas channel, the second liquid channel, the first gas channel and the gas-liquid channel, and
   keeping the second valve, the third valve, and the sixth valve closed;
during a second time period associated with adding the unused culture medium from the first container to the second container,
   opening the second valve, the third valve, and the fifth valve to allow flow in a second direction through the second gas channel, the first liquid channel, and the gas-liquid channel, and
   keeping the sixth valve, the seventh valve, the fourth valve, and the first valve closed; and
during a third time period associated with adding humidified gas to the second container from the gas supply source via the humidifying bottle, the first connection portion, and the first gas channel,
   opening the first valve and the fifth valve to allow flow in the second direction through the first gas channel and the gas-liquid channel, and
   keeping the seventh valve, the fourth valve, the second valve, the sixth valve, and the third valve closed.

6. The method of claim 5, further comprising:
during a fourth time period associated with clearing the culture medium from the gas-liquid channel into the second container,
   opening the first valve and the fifth valve to allow flow in the second direction through the first gas channel and the gas-liquid channel, and
   keeping the second valve, the third valve, the sixth valve, the seventh valve, the fourth valve, and the third valve closed; and
during a fifth time period associated with clearing the culture medium from the first liquid channel into the second container,
   opening the third valve and the first valve to allow flow in a third direction opposite to the second direction through the first liquid channel, and
   keeping the second valve, the sixth valve, the seventh valve, the fourth valve, and the fifth valve closed.

7. The method of claim 6, wherein the cell culture device is the cell culture device of claim 4, the method further comprising:
during a pressure normalization operation after each of the first time period and the third time period,
   opening the sixth valve to allow flow in a fourth direction from the humidifying bottle to the outside air through the first branched portion of the branched gas channel and the third branched portion of the branched gas channel, and
   keeping the second valve, seventh valve, the fourth valve, the third valve, the first valve, and the fifth valve closed.

8. The method of claim 7, further comprising:
during a pressure normalization operation after the fifth time period,
   opening the second valve and the sixth valve to allow flow in a fifth direction opposite to the second direction from the first container to the outside air through the second gas channel, the second connection portion, the second branched portion of the branched gas channel, and the third branched portion of the branched gas channel, and
   keeping the first valve, the third valve, the fourth valve, the fifth valve, and the seventh valve closed.

* * * * *